United States Patent [19]

Albrecht et al.

[11] Patent Number: 5,332,714

[45] Date of Patent: Jul. 26, 1994

[54] DEFOAMER FOR LIQUID WETTING AGENTS AND LOW-FOAM LIQUID PLANT PROTECTION AGENTS

[75] Inventors: Konrad Albrecht, Kelkheim; Jean Kocur, Hofheim am Taunus, both of Fed. Rep. of Germany

[73] Assignee: Hoechst Aktiengesellschaft, Frankfurt am Main, Fed. Rep. of Germany

[21] Appl. No.: 549,210

[22] Filed: Jul. 6, 1990

[30] Foreign Application Priority Data

Jul. 8, 1989 [DE] Fed. Rep. of Germany ....... 3922500
Jun. 15, 1990 [DE] Fed. Rep. of Germany ....... 4019084

[51] Int. Cl.$^5$ .............. A01N 57/12; A01N 25/30; B01D 19/04
[52] U.S. Cl. .............. 504/116; 504/127; 504/133; 504/141; 504/148; 504/149; 504/204; 504/205; 504/206; 71/DIG. 1; 252/321
[58] Field of Search ............. 71/86, DIG. 1; 252/321, 252/358; 504/204, 205, 206

[56] References Cited

U.S. PATENT DOCUMENTS 3,912,654  10/1975  Heid et al. .................... 252/321
4,400,196  8/1983  Albrecht et al. ................. 71/86

FOREIGN PATENT DOCUMENTS 2110767   9/1972  Fed. Rep. of Germany .
2233941   3/1978  Fed. Rep. of Germany .
3809159   9/1989  Fed. Rep. of Germany .
86/289004 12/1986  Japan .
89/1996   3/1989  South Africa .
1388924   3/1975  United Kingdom .

Primary Examiner—Allen J. Robinson
Assistant Examiner—B. Bembenick
Attorney, Agent, or Firm—Curtis, Morris & Safford

[57] ABSTRACT

The invention relates to defoamed aqueous solutions of surfactants and to low-foam concentrated liquid preparations of plant protection agents, which contain sulfato- or sulfonato-containing surfactants as wetting agents and surfactants from the group comprising the perfluoro($C_6$–$C_{18}$)alkylphosphinic acids and/or -alkylphosphonic acids and/or their salts, as defoamer.

17 Claims, No Drawings

DEFOAMER FOR LIQUID WETTING AGENTS AND LOW-FOAM LIQUID PLANT PROTECTION AGENTS

The invention relates to the use of certain perfluoroalkylphosphinic acids and -phosphonic acids as defoamers for wetting agents which can be employed in spray liquors and concentrated preparations of plant protection agents. In particular, the invention relates to defoamers for liquid herbicidal preparations with high contents of sulfato- and sulfonato-containing wetting agents.

It is known that the action of plant protection agents, in particular of foliar herbicides, can be increased when surface-active substances, in particular wetting agents, are added to the aqueous spray liquors of the plant protection agents before they are used.

Wetting agents reduce the surface tension of the spray liquor. This ensures uniform wetting of the leaf surface and in connection with this fact in many cases an improved uptake of active substance.

On the basis of this property, a large number of products is available in the plant protection agents market, which products are offered as additives to spray liquors and which contain, as wetting agents, mainly the nonionic alkylaryl polyglycol ethers (for example ®Citowett, ®Triton X45, ®Ortho X-47, ®Agral 90, ®Dash).

It has also been disclosed or proposed to increase the action of herbicides by adding anionic sulfato- and sulfonato-containing surfactants; cf. DE-A 3,035,554, JP-A 86/289,004 and German Patent Application P 38 09 159.3. This makes particularly economical use of the herbicides possible.

However, spray liquors and liquid preparations which according to DE-A 3,035,554, JP-A 86/289,004 and P 38 09 159.3 contain very large amounts of anionic surfactants (wetting agents) which increase their action, often still show shortcomings when used.

If, for example, these wetting agents are added to the aqueous spray liquors of plant protection agents in the form of their aqueous solutions, these spray liquors produce so much foam in most cases that they result in uneven spray coatings on the plants and in residues of plant protection agents.

Similar disadvantageous effects can occur when concentrated preparations of plant protection agents are used. This is because the wetting-agent-containing concentrated formulations are usually not applied directly as such, but, depending on the concentrations of active substance and wetting agent in the preparations, only applied in amounts of 2–10 and more liters per hectare after they have been diluted and stirred in 50–1,000 liters of water/ha, with the purpose of improving dosage and distribution. Analogously to the abovementioned spray liquors, the spray liquors obtained after dilution produce so much foam in most cases that they foam over from the spray tank and result in dosage irregularities during spraying, which not only causes losses of active substance but above all makes it impossible to guarantee a consistent good action.

This can often be remedied by using an antifoam as an additive which is separately added to the spray liquors. However, using an additive which is added separately requires the use of a further agent in addition to the plant protection agent and the wetting agent, and this is not liked in practice because of the additional dosage and separate stock keeping which are required.

It is therefore an object to find defoamers for the anionic sulfato- and sulfonato-containing wetting agents, which defoamers show good compatibility with the wetting agents, i.e., which are also stable on storage, and which make possible the use of the wetting agents in aqueous systems, in particular in spray liquors of plant protection agents, without problems.

Another object is to find defoamers which give a clear solution in concentrated liquid preparations of plant protection agents. Defoamers which give solid sediments, oily separation products or marked cloudiness, must be excluded in this connection since they make the preparation look as if decomposition had already started. The defoamer to be found must also remain effective and storage-stable when the preparations are stored for 2–4 years. In addition, the defoamer should be effective enough that amounts in the formulation of up to 5% by weight, preferably 0.1–1% by weight, are sufficient. Larger amounts of defoamer can often be incorporated in solid formulations only. In water- and surfactant-containing liquid preparations, phase separations which give phases which are low in surfactants and high in active substance and phases which are high in surfactants and low in active substances can often be found.

A large number of defoamers is known, and they are described, for example, by H. -F. Fink and G. Koerner in "Ullmanns Enzyklopädie der technischen Chemie [Ullmann's Encyclopedia of Industrial Chemistry]", 4th revised and extended edition, Verlag Chemie, Weinheim, Volume 20, page 411–414, and by W. Schönfeldt in "Grenzflächenaktive Alkylenoxid-Addukte [Interface-active Alkylene Oxide Adducts]", Wissenschaftliche Verlagsgesellschaft MBM, Stuttgart 1973, pages 805–853. When these substances were tested, it was found that a few aqueous preparations of plant protection agents which contain large amounts of sulfato- and sulfonato-containing surfactants, are effective as defoamers, but only when added separately to the diluted aqueous spray liquors which were already foaming. If they are dissolved in the formulations from the outset, or if they are combined at the outset with the sulfato- or sulfonato-containing wetting agents and added to a spray liquor as concentrated aqueous surfactant solution, they remain ineffective, are insoluble, give oily separation products or result in cloudiness. However, a later addition of defoamers to the spray liquor independently of the addition of the wetting agent, or to the spray liquor which contains wetting agents, is disadvantageous and in no way satisfactory. For example, it requires dispatch and handling of an additional pack. If, at a given point in time, it is desired to use part of the pack of the liquid herbicide formulation only, it is furthermore necessary to measure the amounts of antifoam which are suitable in each case when the spray liquor is prepared. The fact that the antifoam must be mixed thoroughly with the sprayable preparation is a further disadvantage. The technical disadvantages mentioned are avoided with the invention.

The invention relates to aqueous preparations which contain an anionic wetting agent from the group comprising the sulfato- or sulfonato-containing surfactants (wetting agents) in combination with a surfactant (defoamer) from the group comprising the perfluoro($C_6$–$C_{18}$)alkylphosphinic acids and/or perfluoro($C_6$–$C_{18}$)alkylphosphonic acids and/or salts thereof.

The combination according to the invention of wetting agent/defoamer can be present as a concentrated aqueous solution which is suitable as an addition for spray liquors of plant protection agents, or can be contained in an aqueous concentrated formulation of plant protection agents. The ratio by weight of wetting agent to defoamer is preferably from 1:1 to 500:1, particularly 10:1 to 200:1, and, in particular, 20:1 to 120:1.

Aqueous solutions of wetting agent and defoamer which are of particular interest are those which contain essentially 2 to 90% by weight, preferably 20 to 60% by weight, of anionic sulfato- or sulfonato-containing surfactants (wetting agents) and 0.05 to 5% by weight, preferably 0.1 to 1% by weight, in particular 0.2 to 0.5% by weight, of salts of perfluoro($C_6$-$C_{18}$)alkylphosphinic acids or -alkylphosphonic acids, and water.

The last-mentioned aqueous solutions are suitable as a wetting agent/defoamer addition to spray liquors of plant protection agents and cause an increased action of the plant protection agents, combined with manipulation of the spray liquors without problems.

Plant protection agents which are suitable are, for example, herbicides, insecticides and fungicides, preferably herbicides.

Examples of herbicides whose spray liquor can be treated with the combination according to the invention of wetting agent/defoamer are glufosinate, bialaphos, glyphosate, herbicides from the group comprising the carbamates, thiocarbamates, haloacetanilides, imidazolinones, substituted phenoxy-, naphthoxy-, phenoxy-phenoxy-, benzyloxyphenoxy- and heteroaryloxyphenoxycarboxylic acid derivatives, and also cyclohexanedione derivatives and sulfonyl urea herbicides; examples of heteroaryloxyphenoxycarboxylic acid derivatives are quinolyloxy-, quinoxyloxy-, pyridyloxy-, benzoxazolyloxy- and benzothiazolyloxyphenoxycarboxylic esters. Preferred herbicides are phenoxyphenoxy- and heteroaryloxyphenoxycarboxylic esters. Suitable esters for this purpose are, in particular, lower alkyl, alkenyl and alkynyl esters.

However, the combination according to the invention of wetting agent/defoamer can also be contained in aqueous liquid formulations of the abovementioned herbicides. The invention therefore also relates to liquid herbicidal preparations which contain at least a) one herbicidal active substance, preferably from the group comprising glufosinate, bialaphos, glyphosate, fenoxaprop-ethyl, fenoxaprop-P-ethyl, diclofop-methyl, isoproturon, MCPA, imazapyr, imazaquin, imazethapyr, in particular glufosinate, or one of the salts of this active substance, b) an anionic wetting agent from the group comprising the sulfato- or sulfonato-containing surfactants, c) a surfactant from the group comprising the perfluoro-($C_6$-$C_{18}$)alkylphosphinic acids or -alkylphosphonic acids or of the salts of this surfactant, preferably from the group comprising its alkali metal salts, ammonium salts, salts with $C_1$-$C_{18}$-alkylamines, $C_1$-$C_{18}$-alkylamino-oxethylates or ethylenediamine ethoxylates, or mixtures of the surfactants, and d) water.

Concentrated preparations according to the invention which contain at least a) 1 to 45% by weight, preferably 5 to 30% by weight, of herbicidal active substance, b) 1 to 50, preferably 5 to 35%, by weight of sulfato- or sulfonato-containing surfactant, c) 0.05 to 5% by weight, preferably 0.05 to 1% by weight, in particular 0.2 to 0.5% by weight, of a perfluoro($C_6$-$C_{18}$)alkylphosphinic or -alkylphosphonic acid or its salt, or mixtures thereof, and d) water are of particular interest.

The herbicidal active substances are preferably employed in the form of their salts, which have already been mentioned, from the group comprising the alkali metal salts, ammonium salts, lower or long-chain alkylammonium salts and alkanolammonium salts, and also the salts with fatty amine ethoxylates. The sodium salts, ammonium salts and isopropylammonium salts are particularly preferred in this context.

The sulfonato- or sulfato-containing surfactants are generally employed in an amount of 0.5 to 8, preferably 0.5 to 5, parts by weight per part by weight of the herbicidal active substances, and they mainly serve for improving the activity of the herbicides. Examples of these anionic wetting agents are described in DE-A 3,035,554, JP-86/289,004 and P 3809159.3. Examples of suitable anionic wetting agents (b) are ($C_{10}$-$C_{18}$)-fatty alcohol polyglycol ether sulfates, ($C_{10}$-$C_{18}$)-fatty alkyl sulfates, ($C_8$-$C_{22}$)-α-olefin sulfonates, ($C_4$-$C_{16}$-alkyl) diphenyl ether sulfonates, ($C_{10}$-$C_{18}$)-fatty alkyl sulfonates, ($C_{10}$-$C_{18}$-fatty alkyl) arylsulfonates, ($C_{10}$-$C_{18}$)-fatty alcohol sulfosuccinic monoesters, ($C_{10}$-$C_{18}$)-fatty alcohol polyglycol ether sulfosuccinic esters, and their salts, such as alkali metal salts, ammonium salts, alkaline earth metal salts, alkylammonium salts or alkanolammonium salts, and also mixtures of the wetting agents which have been mentioned. ($C_{12}$-$C_{16}$)-fatty alcohol polyglycol ether sulfates are particularly suitable, especially as alkali metal salts or ammonium salts. Preferred wetting agents with polyglycol ether chains are those which give a clear solution in water and which have a degree of ethoxylation of 1 to 200, in particular 4 to 15. The anionic wetting agents are commercially available or can be prepared by known processes.

Suitable perfluoroalkyl-group-containing surfactants (component c) are, in particular, perfluoro ($C_6$-$C_{12}$)alkylphosphinic acids and -phosphonic acids and their sodium salts, potassium salts, ammonium salts, $C_{10}$-$C_{18}$-alkylammonium salts, and also salts with $C_{10}$-$C_{18}$-alkylamine ethoxylates and ethylenediamine ethoxylates, such as N,N,N',N'-tetrakis-(2,-hydroxypropyl)-ethylenediamine and N,N,N',N'-tetrakis-(2-hydroxyethyl)-ethylenediamine. The perfluoroalkyl-group-containing surfactants are commercially available, for example ®Fluowet PP (mixture of $C_6$-$C_{12}$-perfluoroalkylphosphinic and -alkylphosphonic acids, Hoechst) or can be prepared by known methods. The perfluoroalkylated phosphinic and phosphonic acids are prepared according to DE-A 2,110,767 (GB-A-1,388,924), by oxidative hydrolysis of perfluoroalkyldiiodophosphone and bis(perfluoroalkyl)iodophosphone; the salts are prepared by neutralizing the acids obtained with the corresponding hydroxides or substituted amines in water or polar organic solvents, such as, for example, alcohols, DMF or NMP, it being preferred for the salts to be employed in dissolved form in this process.

In addition to the sulfato- and sulfonato-containing surfactants and the effective perfluoroalkyl-containing defoamers which have been found, the aqueous solutions which are added to the spray liquors, or the preparations containing plant protection agents, can also contain other customary formulation auxiliaries, such as, for example, nonionic surfactants from the alkyl polyglycol ether series, for example isotridecanol polyglycol ether, nonylphenol polyglycol ether, octylphenyl polyglycol ether or fatty amine ethoxylates, other antifreeze agents, such as ethylene glycol or propylene glycol, propylene glycol monomethyl ether, glycerol, isopropanol and urea, and also other dispersants and emulsifiers, as are listed, for example, in McCutcheon, and organic solvents and fillers, such as water-soluble substances, for example ammonium sulfate, urea, sodium sulfate, sodium sulfite and sodium bisulfite.

Concentrated formulations preferably contain one of the herbicides glufosinate (I), bialaphos (II), glyphosate (III), fenoxaprop-ethyl (IV), fenoxaprop-P-ethyl (D-form of (IV)), diclofop-methyl (V), isoproturon (VI), MCPA (VII), imazapyr (VIII), imazaquin (IX), imazethapyr (X) or mixtures of two or more of the active substances which have been mentioned. The compounds (I) and (III) to (X) are described in "Pesticide Manual", 8th edition (1987), edited by the British Crop Protection Council. The compound (II) (bialaphos) is described in U.S. Pat. No. 4,309,208. The active substances (I) to (III) and (VII) to (X) are generally employed in the form of their sodium, ammonium and monoisopropylammonium salts. In practice, they can also be used in the form of other alkali metal salts or lower alkylammonium salts or alkanolammonium salts, they can also be employed as salts of long-chain $C_8$-$C_{18}$-alkylamines or fatty amine ethoxylates (cf. EP 0,290,416 and German Patent Application P 38 32 147.2).

The preparations according to the invention can additionally also contain other herbicidal active substances, for example f1) other water-soluble herbicidal active substances, such as those from the phenoxy series, such as CMPP, MCPA, 2,4-D or ioxynil or bromoxynil, or their salts, or f2) other solid insoluble active substances, such as herbicides from the urea series, such as diuron, linuron, monolinuron, isoproturon, thidiazuron and/or herbicides of the triazine series, such as simazine, atrazine and/or sulfonylureas, such as DPX-L-5300, thiameturon-methyl (DPX-M-6316) and metsulfuron-methyl (DPX-M 6376), and also N-alkoxy- and N-alkylsulfonylaminosulfonylureas as are mentioned in EP-A 0,131,258, in particular in Examples 17, 18, 19 and 20 to 124, f3) other liquid active substances, or active substances with a low melting point, such as alachlor, metolachlor, trifluralin, esters of the phenoxy herbicides and esters of ioxynil and bromoxynil.

In this context, the active substances of class f1) can be formulated as aqueous solution concentrates, and those of class f2) in the form of suspension concentrates, the concentrates containing water-soluble active substances, such as, for example, active substances (I) to (III), in the aqueous carrier phase and insoluble active substances as ultrafinely-divided solid phase. The active substances of class f3) are to be formulated, for example, as suspoemulsions which contain water-soluble active substances, for example (I) to (III), in the aqueous phase and the liquid active substances, or the active substances with low melting points, in the oily phase, either as such or dissolved in customary solvents, for example from the group comprising the aromatic, optionally halogenated hydrocarbons or aliphatic esters or ketones.

Occasionally, it is advantageous to process compounds of class f2) with water-soluble herbicides (for example herbicides (I) to (III)) and the sulfato- and sulfonato-containing wetting agents to give water-dispersible granules. In this case too, the perfluoroalkylated compounds used according to the invention act as defoamers.

Many of the active substances mentioned under f1), f2) and f3) are known from "Pesticide Manual" (by the British Crop Protection Council), which has already been mentioned. The sulfonylureas DPX-L-5300, DPX-M-6316 and DMX-M-6376 are described in "Farm Chemicals Handbook 89" (Meister Publishing Company, Willoughby, Ohio, 1989).

The defoamers (c) are also effective when they are contained in amounts of preferably 0.05 to 5% by weight, particularly 0.05–1% by weight and in particular 0.2 to 0.5% by weight as a solution in the aqueous solution or dispersion of active substance, and this solution or dispersion of active substance in water is applied, with sulfato- and sulfonato-containing surfactants (c) and optionally other auxiliaries (e), such as, for example, alkyl polyglycol ethers or fatty amine ethoxylates, being added separately to the solution which is then diluted, before application.

The defoamers are also effective when they are contained in amounts of preferably 0.05–5% by weight, in particular 0.05–0.5% by weight, as a solution in the surfactants, and such a surfactant mixture is added to the spray liquors of liquid formulations of the herbicidal active substances.

The invention therefore also relates to the diluted preparations (spray liquors) which contain the components of the abovementioned concentrated preparations in 5× to 500× dilute form.

The invention also relates to the process for preparing the preparations according to the invention, which comprises combining the perfluoro-containing surfactants (c), optionally dissolved in water and optionally together with the anionic wetting agents (b), with the aqueous solution or dispersion of the active substances (a) which optionally already contains anionic wetting agents (b) and/or other active substances (f) and/or customary auxiliaries (e), before or after it is diluted with water or without dilution with water, and, if required, adding other anionic wetting agents (b) or remaining components.

The perfluoroalkyl-containing surfactants (c) used according to the invention make possible the addition of effective defoamers to herbicidally highly-effective preparations, in particular the aqueous liquid preparations of the water-soluble active substances (I), (II) and (III), which contain effective amounts of anionic, sulfato- or sulfonato-containing surfactants. The same is true analogously for the diluted aqueous spray liquors. The herbicidal agents can thus be marketed for use in practice.

In the examples which follow, percentages are based on weight unless otherwise stated.

EXAMPLES

1. To a solution of
18.00 g of glufosinate-ammonium in
41.75 g of water there are added
30.00 g of Na ($C_{12}$–$C_{16}$)alcohol polyglycol ether sulfate (70% strength in water) and
10.00 g of propylene glycol monomethyl ether.

The mixture is stirred at 40° C. until a clear solution has formed. After this,
0.25 g of Fluowet PP (80% strength in water) are added, and stirring is continued for a short time.

2. To a mixture of
   17.0 g of water,
   10.0 g of propylene glycol monomethyl ether and
   0.5g of Fluowet PP (80% strength in water) there are added
   13.5 g of glufosinate-ammonium and
   59.0 g of Na ($C_{12}$–$C_{16}$)alcohol polyglycol ether sulfate (70% strength in water). The mixture is stirred at 40° C. until a solution has formed.
3. To a solution of
   17.00 g of the Na salt of L-2-amino-4-(hydroxy)-(methyl)phosphinoyl butyryl-alanyl-L-alanine in
   52.75 g of water there are added
   20.00 g of Na ($C_{12}$–$C_{16}$)alcohol polyglycol ether sulfate (70% strength in water),
   0.25 g of Fluowet PP (80% strength in water) and
   10.00 g of methylglycol.
   The mixture is stirred at 40° C. until a solution has formed.
4. To a mixture of
   35.50 g of water,
   5.00 g of propylene glycol methyl ether and
   0.50 g of Fluowet PP (80% strength in water) there are added
   29.00 g of glyphosate-isopropylammonium salt (62% strength in water) and
   30.00 g of Na ($C_{12}$–$C_{16}$)alcohol polyglycol ether sulfate (70% strength in water)
   and the mixture is stirred at 25° C. until a solution has formed.
5. To a solution of
   18.6 g of glufosinate-ammonium in
   61.5 g of water there are added
   20.0 g of the disodium salt of isodecylsulfosuccinic monoester.
   The mixture is stirred until a solution has formed.
   0.5 g of Fluowet PP (80% strength in water) is then added, and stirring is continued for a short time.
6. To a solution of
   17.6 g of glufosinate-ammonium in
   43.2 g of water there are added
   24.0 g of the disodium salt of isodecylsulfosuccinic monoester (50% strength in water) and
   14.7 g of Na ($C_{12}$–$C_{16}$)alcohol polyglycol ether sulfate (70% strength in water) and
   0.5 g of Fluowet PP (80% strength in water).
   The mixture is stirred at 40° C. until a solution has formed.

Suspended material in formulations 1 to 6, which can lead to slight cloudiness, can be removed by filtration.

Foam Test

A 250 ml measuring cylinder which can be sealed with a glass stopper is filled with 190 ml of standard water D (342 ppm hardness in accordance with CIPAC Handbook I, p 878), and 10 ml of the formulation to be tested are added.

The sealed cylinder is turned 10 times by 180° and back. A stopwatch is started immediately afterwards to measure the time which elapses until the foam has collapsed.

Result

When formulations are used which contain the defoamers according to the invention, 90% of the foam disappears within 1 minute, and often all of the foam collapses within 30 s.

When formulations are used which do not contain defoamer, the foam often remains stable for more than 1 h. Analogously to Examples 1 to 6, it is also possible to employ, in place of perfluoroalkylphosphinic acid/-phosphonic acid (Fluowet PP), those salts of this acid which have good solubility in water and/or organic solvents.

The salts are advantageously employed in dissolved form with 0.05 to 1.0% by weight of acid equivalent, preferably with 0.2 to 0.5% by weight of acid equivalent. However, they can also be formed during the formulation process by neutralization with the corresponding bases. Formulations are prepared analogously to Examples 1 to 6 with the salts of ®Fluowet PP which were prepared in Examples 7 to 9, and a correspondingly good defoamer action is observed.

7. Salt of Fluowet PP with coconut fatty amine+2 EO
   To a solution of
   29.50 g of coconut fatty amine+2 EO (EO=ethyleneoxy unit) in
   29.50 g of propylene glycol monomethyl ether there is run in slowly with stirring a solution of
   51.90 g of Fluowet PP (80% strength in water) in
   31.14 g of propylene glycol monomethyl ether.
   In this way, a solution which contains 50% by weight of the Fluowet PP salt and which has a pH of 6.9 is obtained.

8. Salt of Fluowet PP with triethanolamine
   To a solution of
   51.90 g of Fluowet PP (80% in water) in
   31.14 g of water there is run in slowly with stirring a solution of
   14.92 g of triethanolamine in
   14.92 g of water.
   In this manner, a solution which contains 50% by weight of the Fluowet PP salt and which has a pH of 6.8 is obtained.

9. Salt of Fluowet PP with N,N,N',N'-tetrakis--(2-hydroxypropyl)-ethylenediamine*
   To a solution of
   51.90 g of Fluowet PP (80% strength in water) and
   31.14 g of propylene glycol monomethyl ether there is run in slowly with stirring a solution of
   21.90 g of HOE S 3528 in
   21.90 g of propylene glycol monomethyl ether.
   In this way, a solution which contains 50% by weight of the Fluowet PP salt and which has a pH of 6.4 is obtained.
   *HOE S-3528 (Hoechst) or ®Quadrol L (BASF)

10. Salt of Fluowet PP with ®Genamin T 150
    To a solution of
    50.79 g of propylene glycol monomethyl ether,
    7.57 g of polyethylene glycol 600 and
    26.57 g of tallow fatty amine ethoxylate (Genamin T 150)
    there are run in slowly with stirring
    15.07 g of Fluowet PP (80% strength in water).
    A slightly cloudy solution which has a pH of 6.8 is formed. Most of the cloudiness settles after the mixture has been allowed to stand for 24 h. Before the mixture is added to aqueous surfactant solutions, it is again stirred briefly.

11. Example of defoaming of surfactant solutions when used in aqueous spray liquors
    To 98.72 g of Na $C_{12}$-$C_{14}$-alkyl diglycol ether sulfate (28% strength in water, ®Genapol LRO liquid, Hoechst) there are added 1.28 g of the N,N,N',N'-tetrakis-2-(hydroxypropyl)e-thylenediamine salt of Fluowet PP, 50% strength in propylene glycol monomethyl ether, from Example 9, and the mixture is stirred briefly. The result is a clear solution. If, in a 250 ml standard cylinder, 10 g of this solution are diluted with 230 g of water and 2 g of glufosinate-ammonium (50% strength in water) are subsequently added, the foam which has formed after the sealed cylinder has been turned through 180° and back 10 times collapses within 1 minute.

12. Other examples of defoaming of surfactant solutions when used in aqueous spray liquors Surfactant solution A:

To 98.6 g of Na $C_{12}$–$C_{14}$-alkyl diglycol ether sulfate (28% strength in water, ®Genapol LRO liquid, Hoechst)

there were added 1.4 g of the Fluowet PP/Genamin T 150 salt from Example 10. Brief stirring results in a clear solution which is ready for use.

Surfactant solution B:

To 98.6 g of Na alpha-olefin sulfonate (40% strength in water, ®Hostapur OS, Hoechst)

there are added 1.4 g of the Fluowet PP/Genamin T 150 salt from Example 10, and the mixture is stirred until a homogeneous solution has formed which is slightly cloudy.

Surfactant solution C:

To 98.6 g of Na alkanesulfonate (30% strength in water, ®Hostapur SAS, Hoechst)

there are added 1.4 g of the Fluowet PP/Genamin T 150 salt from Example 10, and the mixture is stirred briefly until a homogeneous solution has formed which is slightly cloudy.

Surfactant solution D:

To 98.6 g of disodium isodecylsulfosuccinic monoester (30% strength in water, ®Netzer iS, Hoechst)

there are added 1.4 g of the Fluowet PP/Genamin T 150 salt from Example 10, and stirring is continued for a short time.

The solutions of the surfactants were tested with the standard formulations of the plant protection agents glufosinate (®Basta, Hoechst, 200 g of active substance per liter)

fenoxyprop-P-ethyl (®Puma Super, Hoechst, 75 g of active substance per liter)

isoproturon (®Arelon liquid, Hoechst, 500 g of active substance per liter)

diclofopmethyl (®Illoxan, Hoechst 378 g of active substance per liter)

by mixing 5 ml portions of the plant protection agent formulation in question (PPA) with 10 ml portions of a surfactant solution in a 250 ml standard cylinder with 185 ml of water (standard water D in accordance with CIPAC Handbook 1970, p. 878) in such a way that the sealed cylinder was turned 10 times by 180° and back and the time which had elapsed until the foam had collapsed was measured. The results are compiled in the table below:

| PPA | Surfactant solution | | | |
|---|---|---|---|---|
| | A | B | C | D |
| Basta | 45 sec | 2 min | 1 min | 1 min |
| Puma Super | 30 sec | 2 min | 3 min | 30 sec |
| Arelon liquid | 30 sec | 3 min | 2 min | 1 min |
| Illoxan | 30 sec | 3 min | 1 min | 30 sec |

It can be seen from the table that the foam collapses within 30 sec to 3 min.

If the test is carried out with the surfactant solutions which do not contain defoamer, the time required until the foam collapses is mostly more than 10 min.

13. Defoamer test (with Comparison Examples)

To a clear solution which contains 20% by weight of glufosinate-ammonium salt and 20% by weight of Na ($C_{12}$–$C_{16}$)-fatty alcohol ether sulfate there are added commercially available defoamers as a comparison with ®Fluowet PP. Depending on the effectiveness and solubility, up to 5% by weight of defoamer are added, in the case of silicones and fluorinated substances about 0.2 to 0.3% by weight. The defoaming action or the foaming behavior is tested after the mixture has been diluted to give a spray liquor containing 2% by weight of glufosinate-ammonium (see Table 1). As shown in Table 1, the substances which are marketed as defoamers are not effective when they are incorporated at the outset into the active substance preparations containing anionic surfactants. Moreover, most of the antifoam agents do not give a clear solution. A few of those which are soluble lose their activity when the herbicidal preparations are stored. The defoamers tested here are known and have different chemical structures. Since the suppliers only reveal the chemical composition to a certain extent, the tradenames of the defoamers, the manufacturers and the chemical group to which they belong are listed in Table 1.

One of the surprising observations is that perfluoroalkyl-containing surfactants other than those according to the invention do not have a good defoamer action in the test.

Analogous results are obtained in comparison experiments in which glufosinate-ammonium has been replaced by glyphosate and bialaphos.

TABLE 1

Defoamer test of aqueous glufosinate formuations with high contents of anionic wetting agents

| Serial no. | Tradename | Supplier | Chemical active ingredient | Solubility in Basta-Forsul | Defoaming action after storage of the formulation at 50° C. | | | |
|---|---|---|---|---|---|---|---|---|
| | | | | | immed. | 1 month | 2 months | 3 months |
| 1 | Entschäumer TIP | Hoechst AG | triisobutyl phosphate in isobutanol | cloudy | none | — | — | — |
| 2 | Entschäumer KH | Hoechst AG | non-ionic compound | clear | none | — | — | — |
| 3 | Entschäumer SF | Hoechst AG | neutralized mixture of phosphinic/phosphonic acids | clear | none | — | — | — |
| 4 | Antischaum-pulver SP 3 | Wacker | based on siloxane | clear | good | — | — | — |
| 5 | Antischaum-pulver SP 8 | Wacker | siloxane + polyvinyl alcohol + silica | virtually insoluble | good | poor | no action | — |
| 6 | Schaumstopp | Wacker | polydimethyl siloxane | cloudy | good | good | poor | no action |
| 7 | Hoe S 3181 | Hoechst AG | mineral-oil-free | cloudy | none | | | |

TABLE 1-continued

Defoamer test of aqueous glufosinate formulations with high contents of anionic wetting agents

| Serial no. | Tradename | Supplier | Chemical active ingredient | Solubility in Basta-Forsul | Defoaming action after storage of the formulation at 50° C. | | | |
|---|---|---|---|---|---|---|---|---|
| | | | | | immed. | 1 month | 2 months | 3 months |
| | | | defoamer | | | | | |
| 8 | Entschäumer STE | Wacker | polydimethylsiloxane | clear | good | no action | — | — |
| 9 | Entschäumer SRE | Wacker | polydimethylsiloxane | clear | good | poor | no action | — |
| 10 | Hoe S 2736 | Hoechst AG | 85% polyglycol + perfluoroethanol + isononanoic acid amide | cloudy | none | — | — | — |
| 11 | Entschäumer KS 1 | Hoechst AG | — | clear | none | — | — | — |
| 12 | Fluowet PP | Hoechst AG | perfluorinated alkyl-phosphinic/phosphonic acid | clear | v. good | v. good | v. good | v. good |
| 13 | Nopco KX 2 | Diamond Shamrock | siloxane + aliphatic hydrocarbons | clear | none | — | — | — |
| 14 | Nopco NDW | Diamond Shamrock | siloxane + aliphatic hydrocarbons | cloudy | none | — | — | — |
| 15 | Anitschaum-mittel 5882 | Wacker | based on siloxane | cloudy | none | — | — | — |
| 16 | Antischaum-mittel 5155 | Wacker | based on siloxane | cloudy | good | good | no action | — |
| 17 | Antischaum-mittel SLÄ 54289 | Wacker | based on siloxane | clear | good | poor | no action | — |
| 18 | Entschäumer RD | Dow/Corning | based on siloxane | virtually clear | good | poor | no action | — |
| 19 | RD-Emulsion 500 CC | Dow/Corning | based on siloxane | clear | none | — | — | — |
| 20 | Entschäumer DB 31 | Dow/Corning | based on siloxane | clear | good | good | poor | no action |
| 21 | Entschäumer MSA | Dow/Corning | based on siloxane | cloudy | good | good | no action | — |
| 22 | Entschäumer DB 100 | Dow/Corning | based on siloxane | cloudy | poor | no action | — | — |
| 23 | Entschäumer Q2-3/68 | Dow/Corning | based on siloxane | insoluble | none | — | — | — |
| 24 | Surflon S-111 | Asaki Chem. | perfluoroalkyl carboxylic acid | clear | none | — | — | — |
| 25 | Surflon S-112 | Asaki Chem. | perfluoroalkyl phosphate | clear | none | — | — | — |
| 26 | Surflon S-121 | Asaki Chem. | perfluoroalkyl tri-methylammonium salt | clear | none | — | — | — |
| 27 | Surflon S-131 | Asaki Chem. | perfluoroalkyl betaine | clear | none | — | — | — |
| 28 | Surflon S-141 | Asaki Chem. | perfluoroalkyl poly-glycol ether | clear | none | — | — | — |
| 29 | Surflon S-145 | Asaki Chem. | perfluoroalkyl poly-glycol ether | clear | none | — | — | — |
| 30 | K-Palmital | | soap | cloudy | none | — | — | — |
| 31 | Mg-Stearat | | soap | cloudy | none | — | — | — |
| 32 | Entschäumer Q 75 | SWS-Silcone's | based on siloxane | virtually insoluble | none | — | — | — |
| 33 | Entschäumer Q 93 | " | based on siloxane | virtually insoluble | none | — | — | — |
| 34 | Entschäumer Q 94 | " | based on siloxane | virtually insoluble | none | — | — | — |
| 35 | Entschäumer Q 101 | " | based on siloxane | virtually insoluble | none | — | — | — |
| 36 | Entschäumer SWS 203 | " | based on siloxane | virtually insoluble | none | — | — | — |
| 37 | Entschäumer SWS 211 | " | based on siloxane | virtually insoluble | none | — | — | — |
| 38 | Entschäumer SWS 213 | " | based on siloxane | virtually insoluble | none | — | — | — |
| 39 | Entschäumer Q2-3241 | Dow Corning | based on siloxane | insoluble | none | — | — | — |
| 40 | Entschäumer Q2-3242 | " | based on siloxane | insoluble | good | cannot be employed, cloudy | | |
| 41 | Entschäumer DB 110 A | Dow Corning | based on siloxane | cloudy | none | — | — | — |
| 42 | Entschäumer 1520 | " | based on siloxane | cloudy | none | — | — | — |
| 43 | Antimoussol 454 | Rhône Poulenc | based on siloxane | oily separation product | none none | — — | — — | — — |
| 44 | Antimoussol 416 | " | based on siloxane | oily separation product | none none | — — | — — | — — |
| 45 | Antimoussol 426 R | " | based on siloxane | oily separation product | none good | — cannot be used | — | — |
| 46 | Antimoussol 20417 | " | modified silicone oil | insoluble | none | — | — | — |
| 47 | Foammaster D01 | Diamond Shamrock | silicone emulsion | insoluble | none | — | — | — |

TABLE 1-continued

Defoamer test of aqueous glufosinate formuations with high contents of anionic wetting agents

| Serial no. | Tradename | Supplier | Chemical active ingredient | Solubility in Basta-Forsul | Defoaming action after storage of the formulation at 50° C. | | | |
|---|---|---|---|---|---|---|---|---|
| | | | | | immed. | 1 month | 2 months | 3 months |
| 48 | Foammaster UD8 | Diamond Shamrock | silicone emulsion | cloudy | none | — | — | — |
| 49 | Polysekon 133 | Goldschmidt | based on siloxane | clear | none | — | — | — |
| 50 | Polysekon 720 | Goldschmidt | based on siloxane | clear | none | — | — | — |
| 51 | Beraloid 6420 | Erbslöh | "polymer substance" | clear | none | — | — | — |
| 52 | Beraloid 581 B | Erbslöh | metal soaps | clear | none | — | — | — |
| 53 | Beraloid 5581 | Erbslöh | no silicone oil, no further information | clear | none | — | — | — |
| 54 | Dehypon LT 24 | Henkel | fatty alcohol EO pyoglycol | clear | none | — | — | — |
| 55 | Dehydran | Henkel | based on siloxane | clear | good | poor | no action | — |
| 56 | Dehydran 131 | Henkel | mixture of fatty acid esters and silicone oil | cloudy | none | — | — | — |
| 57 | Dahydran 240 | Henkel | modified polyethylene glycol | clear | none | — | — | — |
| 58 | Dehydran 242 | Henkel | based on siloxane | clear | none | — | — | — |
| 59 | Dehydran 243 | Henkel | based on siloxane | clear | none | — | — | — |
| 60 | Dehydran 490 | Henkel | "hydroxyl-containing" | clear | none | — | — | — |
| 61 | Cetiel HE | Henkel | unknown | clear | none | — | — | — |
| 62 | Versuchs produkt KE 1445 | Henkel | unknown | clear | none | — | — | — |
| 63 | Entschäumer KE 1393 | Henkel | polyglycerol + 22 PgO | clear | none | — | — | — |
| 64 | Entschäumer KE 1102 A | Henkel | unknown | clear | none | — | — | — |
| 65 | Entschäumer BE 7249 | Henkel | unknown | clear | none | — | — | — |
| 66 | Entschäumer K 975 | Henkel | unknown | clear | none | — | — | — |
| 67 | Antimoussol A6 | Sandoz | glycerol dialkyl ether | clear | none | — | — | — |
| 68 | Antimoussol WLN | Sandoz | glycerol dialkyl ether + wetting agent | clear | none | — | — | — |
| 69 | Rheolate | unknown | unknown | cloudy | none | — | — | — |
| 70 | Elenor C 22 R | unknown | unknown | cloudy | none | — | — | — |

We claim:

1. An aqueous preparation which contains an anionic wetting agent selected from the group consisting of the sulfato- or sulfonato-containing surfactants (wetting agents) in combination with a surfactant (defoamer) selected from the group consisting of salts of perfluoro($C_6$-$C_{18}$)alkylphosphinic or -phosphonic acids with $C_1$-$C_{18}$-alkylamines, $C_1$-$C_{18}$-alkylamino-oxyethylates or ethylene diamine ethoxylates or mixtures of the defoamers.

2. An aqueous preparation as claimed in claim 1, containing wetting agent and defoamer in a ratio by weight of 1:1 to 500:1.

3. An aqueous preparation as claimed in claim 1, comprising 2 to 90% by weight of wetting agent, 0.05 to 5% by weight of defoamer and water.

4. A preparation as claimed in claim 1, containing, as the sulfato- or sulfonato-containing surfactant, a ($C_{10}$-$C_{18}$)-fatty alcohol polyglycol ether sulfate, a ($C_{10}$-$C_{18}$)-fatty alkyl sulfate, a ($C_8$-$C_{22}$)-α-olefin sulfonate, a ($C_4$-$C_{16}$-alkyl)diphenyl ether sulfonate, a ($C_{10}$-$C_{18}$)-fatty alkyl sulfonate, a ($C_{10}$-$C_{18}$-fatty alkyl)arylsulfonate, a ($C_{10}$-$C_{18}$)-fatty alcohol sulfosuccinic monoester, a ($C_{10}$-$C_{18}$)-fatty alcohol polyglycol ether sulfosuccinic monoester, or a salt of these, or a mixture of the above surfactants.

5. A preparation as claimed in claim 1, which contains, in addition to the components mentioned, other customary formulation auxiliaries, selected from the group consisting of nonionic surfactants, antifreeze agents, dispersants, emulsifiers, organic solvents and fillers.

6. An aqueous liquid herbicidal preparation comprising:
a) a herbicidally active substance;
b) an anionic wetting agent selected from the group consisting of the sulfato- or sulfonato-containing surfactants;
c) a defoamer which is a surfactant selected from the group consisting of salts of perfluoro($C_6$-$C_{18}$)alkylphosphinic or -phosphonic acids with $C_1$-$C_{18}$-alkylamines, $C_1$-$C_{18}$-alkylamino-oxethylates or ethylene diamine ethoxylates or mixtures of the defoamers; and
d) water.

7. The preparation as claimed in claim 6 comprising:
a) 1 to 45% by weight of the herbicidally active substance;
b) 1 to 50% by weight of the sulfato- or sulfonato-containing surfactant;
c) 0.05 to 5% by weight of a surfactant selected from the group consisting of salts of perfluoro($C_6$-$C_{18}$)alkylphosphinic or -phosphonic acids with $C_1$-$C_{18}$-alkylamines, $C_1$-$C_{18}$-alkylamino-oxethylates or ethylene diamine ethoxylates or mixtures of the defoamers; and
d) water.

8. The preparation as claimed in claim 6, wherein the surfactant is selected from the group consisting of salts of perfluoro($C_6$-$C_{18}$)alkylphosphinic or -phosphonic acids with $C_{10}$-$C_{18}$-alkylamines, $C_{10}$-$C_{18}$-alkylamino-oxyethylates or ethylene diamine ethoxylates or mixtures of the defoamers.

9. The preparation as claimed in claim 7, wherein the surfactant is selected from the group consisting of salts of perfluoro($C_6$–$C_{18}$)alkylphosphinic or -phosphonic acids with $C_{10}$–$C_{18}$-alkylamino-oxyethylates or ethylene diamine ethoxylates or mixtures of the defoamers.

10. The preparation as claimed in claim 6, which comprises an additional herbicidally active substance selected from the group consisting
    a water-soluble herbicidally active substance from the phenoxy series, ioxynil, or bromoxynil, or a salt thereof,
    a solid insoluble herbicide from the urea, triazine or sulfonylurea series, or
    a liquid active substance, or active substance with a low melting point, selected from the group consisting of alachlor, metolachlor, trifluralin, esters of the phenoxy herbicides and esters of ioxynil and bromoxynil.

11. The preparation as claimed in claim 6, wherein the wetting agent and surfactant are present in ratio by weight of 1:1 to 500:1.

12. The preparation as claimed in claim 6, comprising 2 to 90% by weight of wetting agent, 0.05 to 5% by weight of surfactant and water.

13. The preparation as claimed in claim 6 wherein the herbicidally active substance is glufosinate-ammonium.

14. The preparation as claimed in claim 6 wherein the anionic wetting agent is sodium ($C_{12}$–$C_{16}$) alcohol polyglycol ether sulfate.

15. The preparation as claimed in claim 1, which contains as defoamer a surfactant selected from the group consisting of salts of perfluoro($C_6$–$C_{18}$) alkylphosphinic or -phosphonic acids with $C_{10}$–$C_{18}$-alkylamino-oxyethylates or ethylene diamine ethoxylates or mixtures of the defoamers.

16. An aqueous liquid herbicidal preparation comprising:
    a) glufosinate-ammonium;
    b) sodium ($C_{12}$–$C_{16}$) alcohol polyglycol ether sulfate;
    c) a surfactant (defoamer) selected from the group consisting of salts of perfluoro($C_6$–$C_{18}$)alkylphosphinic or -phosphonic acids with $C_1$–$C_{18}$-alkylamines, $C_1$–$C_{18}$-alkylamino-oxyethylates or ethylene diamine ethoxylates or mixtures of the defoamers; and
    d) water.

17. The preparation as claimed in claim 16, which further comprises propylene glycol monomethyl ether.

* * * * *